(12) United States Patent
Boldingh et al.

(10) Patent No.: US 7,381,674 B1
(45) Date of Patent: Jun. 3, 2008

(54) IRIDIUM AND GERMANIUM-CONTAINING CATALYSIS AND ALKYLAROMATIC TRANSALKYLATION PROCESSES USING SUCH CATALYSTS

(75) Inventors: Edwin P. Boldingh, Arlington Heights, IL (US); Maureen L. Bricker, Buffalo Grove, IL (US); Robert B. Larson, Chicago, IL (US); Frank S. Modica, Naperville, IL (US); James E. Rekoske, London (GB)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 11/460,645

(22) Filed: Jul. 28, 2006

(51) Int. Cl.
*B01J 29/06* (2006.01)
(52) U.S. Cl. .................. 502/60; 502/73; 502/74; 502/78
(58) Field of Classification Search ........... 502/60, 502/73, 74, 78
See application file for complete search history.

(56) References Cited

U.S. PATENT DOCUMENTS

| | | | |
|---|---|---|---|
| 3,562,345 A | 2/1971 | Mitsche | |
| 3,617,510 A * | 11/1971 | Hayes | 208/111.05 |
| 3,644,198 A * | 2/1972 | Wilhelm | 208/111.1 |
| 3,900,386 A * | 8/1975 | Hayes | 208/111.1 |
| 3,951,868 A | 4/1976 | Wilhelm | |
| 4,331,822 A | 5/1982 | Onodera et al. | 585/482 |
| 4,623,632 A * | 11/1986 | Lambert et al. | 502/74 |
| 5,106,801 A * | 4/1992 | Zones et al. | 502/64 |
| 5,185,306 A * | 2/1993 | Cohn et al. | 502/66 |
| 5,736,478 A * | 4/1998 | Cortright et al. | 502/74 |
| 5,847,256 A | 12/1998 | Ichioka et al. | 585/470 |
| 5,952,258 A * | 9/1999 | Saitoh et al. | 502/61 |
| 6,060,417 A | 5/2000 | Kato et al. | 502/66 |
| 6,150,292 A | 11/2000 | Merlen et al. | 502/66 |
| 6,359,184 B1 | 3/2002 | Kato et al. | 585/321 |
| 6,465,705 B1 | 10/2002 | Merlen et al. | 585/481 |
| 6,486,372 B1 * | 11/2002 | Merlen et al. | 585/467 |
| 6,613,709 B1 | 9/2003 | Merlen et al. | 502/64 |
| 6,815,570 B1 * | 11/2004 | Negiz et al. | 585/475 |
| 6,855,854 B1 | 2/2005 | James, Jr. | 585/323 |
| 6,864,203 B2 * | 3/2005 | Hendriksen et al. | 502/67 |
| 6,864,400 B2 | 3/2005 | Merlen et al. | 585/475 |
| 6,872,866 B1 | 3/2005 | Nemeth et al. | 585/481 |
| 6,958,305 B2 * | 10/2005 | Verduijn et al. | 502/67 |
| 2005/0031535 A1* | 2/2005 | Mueller et al. | 423/716 |

OTHER PUBLICATIONS

Robert A. Meyers, *Handbook of Petroleum Refining Processes*, 2d. Edition, 1997, Part 2, no month.

* cited by examiner

*Primary Examiner*—Elizabeth D. Wood
(74) *Attorney, Agent, or Firm*—Maryann Maas

(57) ABSTRACT

Transalkylation catalysts comprising acidic molecular sieve, iridium and germanium have good activities and attenuate aromatic ring saturation and lights co-production where high atomic ratios of germanium to iridium are present.

10 Claims, No Drawings

IRIDIUM AND GERMANIUM-CONTAINING CATALYSIS AND ALKYLAROMATIC TRANSALKYLATION PROCESSES USING SUCH CATALYSTS

FIELD OF THE INVENTION

This invention relates to improved catalysts and processes for transalkylation of alkylaromatics. The catalysts contain iridium and certain amounts of germanium to provide low ring loss yet achieve desirable conversions with attractive catalyst selectivities.

BACKGROUND OF THE INVENTION

The xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers.

A prior art aromatics complex flow scheme has been disclosed by Meyers in Part 2 of the Handbook of Petroleum Refining Processes, 2d. Edition, in 1997 published by McGraw-Hill.

In general, a xylene production facility can have various types of processing reactions. One is a transalkylation in which benzene and/or toluene are reacted with $C_9+$ aromatics to form more methylated aromatics. Another is xylene isomerization, which may also include dealkylation, where a non-equilibrium mixture of xylenes is isomerized. And another is the disproportionation of toluene to yield one mole of benzene per mole of xylene produced.

In the transalkylation process, adverse side reactions can occur. For instance, the aromatic ring may become saturated or even cleaved resulting in naphthene co-production. The co-production of these non-aromatics, of course, results in a loss of valuable aromatics. Moreover, benzene is often a sought co-product from a xylene production facility. As some of the naphthenes have similar boiling points to benzene, they are not readily removed to achieve a benzene product of sought purity for commercial applications which frequently demand a benzene product having at least a 99.85 percent purity.

Accordingly, a need exists for catalysts and processes for the transalkylation of alkylaromatics, which processes have desirable selectivity of conversion to the desired alkylaromatics such as xylenes, yet at sufficiently high rates of conversion to be commercially feasible.

U.S. Pat. No. 3,562,345 (Mitsche) discloses catalysts for transalkylation or disproportionation of alkylaromatics comprising aluminosilicates such as mordenite. Catalytically active metals such as groups VIB and VII metals may be present.

U.S. Pat. No. 3,951,868 (Wilhelm) discloses catalysts for hydrocarbon conversions comprising a platinum group metal and indium with optionally a Group IVA component such as germanium or tin.

U.S. Pat. No. 4,331,822 (Onodera, et al.) discloses catalysts for xylene isomerization containing molecular sieve such as ZSM-5, platinum and at least one metal from the group of titanium, chromium, zinc, gallium, germanium, strontium, yttrium, zirconium, molybdenum, palladium, tin, barium, cesium, cerium, tungsten, osmium, lead, cadmium, mercury, indium, lanthanum, beryllium, lithium and rubidium.

U.S. Pat. No. 5,847,256 (Ichioka et al.) discloses a process for producing xylene from a feedstock containing $C_9$ alkylaromatics with ethyl-groups over a catalyst containing a zeolite component that is preferably mordenite and with a metal component that is preferably rhenium.

U.S. Pat. No. 6,060,417 (Kato, et al.) discloses catalysts and processes for transalkylation of alkylaromatics wherein the catalysts comprise mordenite, inorganic oxide and/or clay and at least one metal component of rhenium, platinum and nickel. See also, U.S. Pat. No. 6,359,184 (Kato, et al.).

U.S. Pats. Nos. 6,150,292 and 6,465,705 (Merlen, et al.) disclose a xylene isomerization process using a mordenite-containing catalyst that further contains at least one platinum group metal and at least one metal from group III of the periodic table such as gallium, indium or thallium and optionally at least one metal from group IV of the periodic table such as germanium, tin or lead.

U.S. Pats. Nos. 6,613,709 and 6,864,400 (Merlen, et al.) disclose a transalkylation catalyst containing zeolite NES and at lease one metal selected from group VIIB, group VIB and iridium with optionally at least one metal selected from groups III and IV of the periodic table, preferably indium and tin.

U.S. Pat. No. 6,855,854 (James, Jr.) discloses a process using two transalkylation catalysts to react $C_9+$ aromatics with benzene. The catalyst comprises zeolite and optional metal components such as IUPAC 8-10 metal and modifier such as tin, germanium, lead, indium, and mixtures thereof.

U.S. Pat. No. 6,872,866 (Nemeth, et al.) discloses a liquid phase xylene isomerization process which uses a zeolite beta and pentasil-type zeolite. The catalyst can contain a hydrogenation metal component such as a platinum group metal and modifiers such as rhenium, tin, germanium, lead, cobalt, nickel, indium, gallium, zinc, uranium, dysprosium, thallium, and mixtures thereof.

SUMMARY OF THE INVENTION

In accordance with this invention, iridium-containing catalysts are provided that exhibit desirable transalkylation activities and selectivities with relatively low co-production of lights and non-aromatic benzene coboilers. As used herein, the term transalkylation is intended to include transalkylation between and among alkylaromatics as well as between benzene and alkylaromatics. By this invention, it has been found that in the presence of certain proportions of germanium to iridium, the adverse catalytic properties of iridium in a transalkylation catalyst such as ring saturation, ring cleavage, lights co-production can be substantially attenuated. It is believed that the interaction between iridium and germanium in enhancing transalkylation catalytic properties is unique among the platinum group metals.

In one broad aspect, the catalysts of this invention comprise a catalytically effective amount of acidic molecular sieve, at least about 0.01, preferably less than about 0.3, and more preferably between about 0.05 and 0.25, mass percent iridium calculated on an elemental basis, and a sufficient atomic ratio of germanium to iridium to achieve, under Evaluation Conditions, a Ring Loss of less than about 1.25 mass percent. Often the atomic ratio of germanium to iridium is at least about 5:1, say, 5:1 to 50:1, and preferably between about 8:1 to 40:1.

Evaluation Conditions are:

| Feedstock (+/−0.5%-mass): | |
| --- | --- |
| Toluene: | 75%-mass |
| Trimethylbenzene: | 10%-mass |
| Methylethylbenzene: | 10%-mass |
| Propylbenzene: | 2%-mass |
| Dimethylethylbenzene: | 1%-mass |
| Diethylbenzene: | 0.5%-mass |
| Tetramethylbenzene: | 0.5%-mass |
| Other alkylaromatics and benzene: | balance |
| Pressure: | 1725 kPa (absolute) |
| WHSV, hr$^{-1}$: | 4 |
| H$_2$:HC: | 6 |
| Overall Conversion: | 30%-mass |

Ring Loss is determined as the difference between the mass of total aromatics in the feed to the transalkylation reactor and the mass of total aromatics in the effluent from the alkylation reactor expressed in mass percent. H$_2$:HC is the hydrogen to hydrocarbon mole ratio. Overall conversion is the weighted average conversion of the compounds in the feed.

Another aspect of the transalkylation catalysts of this invention comprises a catalytically effective amount of acidic molecular sieve, a catalytically effective amount of iridium said amount being less than about 0.3 mass percent iridium calculated on an elemental basis, and germanium in an atomic ratio of germanium to iridium of at least about 5:1.

One broad aspect of the transalkylation processes of this invention comprises subjecting a transalkylation feed stream comprising lighter aromatics and heavier aromatics to transalkylation conditions including the presence of transalkylation catalyst comprising a catalytically effective amount of acidic molecular sieve, a catalytically effective amount of iridium, and germanium wherein the atomic ratio of germanium to iridium is sufficient to provide a Ring Loss in the transalkylated product of less than about 1.25 mass percent.

In another aspect, the transalkylation processes of this invention comprise subjecting a transalkylation feed stream comprising lighter aromatics and heavier aromatics to transalkylation conditions including the presence of transalkylation catalyst comprising a catalytically effective amount of acidic molecular sieve, a catalytically effective amount of iridium, and germanium wherein the atomic ratio of germanium to iridium is at least about 5:1.

DETAILED DESCRIPTION OF THE INVENTION

The Process

The processes of this invention comprise transalkylation between lighter (non- or less substituted) aromatics and heavier, greater substituted alkylaromatics with the product being alkylaromatics having the number of substitutions between those of the lighter fraction and those of the heavier fraction. The lighter aromatics have 0 to 2 substitutions and the heavier aromatics have 2 to 5 substitutions with the product falling in between. For example, benzene may be transalkylated with methylethylbenzene to provide toluene and ethylbenzene. Similarly, benzene or toluene may be transalkylated with trimethylbenzene to provide xylene. In some instances for xylene production facilities, it may be desired to consume benzene in the transalkylation rather than producing it as a co-product in which case benzene may comprise from 5 to 80, preferably 10 to 60, mass percent of the lighter aromatics.

Thus the feedstream to the present process generally comprises alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. Suitable alkylaromatic hydrocarbons include, for example but without so limiting the invention, benzene, toluene, ortho-xylene, meta-xylene, para-xylene, ethylbenzene, ethyltoluenes, propylbenzenes, tetramethylbenzenes, ethyldimethylbenzenes, diethylbenzenes, methylpropylbenzenes, ethylpropylbenzenes, triethylbenzenes, di-isopropylbenzenes, and mixtures thereof.

Where the sought product is xylenes or ethylbenzene, the feed stream preferably comprises as the lighter fraction, at least one of benzene and toluene and as the heavier fraction, at least one $C_9+$ aromatic compounds. The molar ratio of benzene and toluene to $C_9+$ aromatics is preferably from about 0.3:1 to about 10:1 and even more preferably from about 0.4:1 to about 6:1. A preferred component of the feedstock where the sought product is xylenes is a heavy-aromatics stream comprising $C_9+$ aromatics. $C_{10}+$ aromatics also may be present, typically in an amount of 50 wt-% or less of the feed. The heavy-aromatics stream generally comprises at least about 90 wt-% aromatics.

The feedstock is preferably transalkylated in the gas-phase and in the presence of hydrogen. If the feedstock is transalkylated in the gas-phase, then hydrogen is added, commonly in an amount of from about 0.1 moles per mole of alkylaromatics up to 10 moles per mole of total aromatic compounds in the feed. This ratio of hydrogen to aromatic compound is also referred to as hydrogen to hydrocarbon ratio. If the transalkylation is conducted in the liquid phase, it is usually done in a substantial absence of hydrogen beyond what may already be present and dissolved in a typical liquid aromatics feedstock. In the case of partial liquid phase, hydrogen may be added in an amount less than 1 mole per mole of alkylaromatics.

Transalkylation conditions typically comprise elevated temperature, e.g., from about 100° C. to about 540° C., preferably, from about 200° C. to about 500° C. Often, in commercial facilities, the transalkylation temperature is increased to compensate for any decreasing activity of the catalyst. The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors containing catalyst of this invention.

The reactors may be of any suitable type and configuration. The use of a single reaction vessel having a fixed cylindrical bed of catalyst is preferred, but other reaction configurations utilizing moving beds of catalyst or radial-flow reactors may be employed if desired.

Transalkylation conditions include pressures ranging from about 100 kPa to about 6 MPa absolute, preferably from about 0.5 to about 5 MPa absolute. The transalkylation reaction can be effected over a wide range of space velocities. The weight hourly space velocity (WHSV) generally is in the range of from about 0.1 to about 20 hr$^{-1}$ preferably from about 0.5 to about 15 hr$^{-1}$, and most often between about 1 to about 5 hr$^{-1}$.

Advantageously, the transalkylation is conducted for a time and under other conditions sufficient that at least about 10, preferably at least about 20, and often between about 20 and 45, mole percent of the heavier alkylaromatic is consumed. Preferably, of the heavier alkylaromatics consumed, at least about 70, most preferably at least about 75, mole percent are converted to lower molecular weight aromatics. The preferred transalkylation products are xylenes for a xylene production facility.

The effluent from the transalkylation typically contains, in addition to the transalkylation product, unreacted lighter and heavier aromatics. Co-products such as naphthenes and lights will also be present. Typically this effluent is normally cooled by indirect heat exchange against the feed to the reaction zone and then further cooled through the use of air or cooling water. The effluent may be subjected to distillation in which substantially all $C_5$ and lighter hydrocarbons present in the effluent are provided in an overhead stream and removed from the process. In the same or a different distillation, at least a portion of the unreacted lights are recovered for recycle. A transalkylation product fraction can be withdrawn, and a heavies stream provided. All or a portion of the heavies stream may be recycled to the transalkylation zone. All or a portion of the lighter aromatics can be recycled to the transalkylation zone.

The Catalyst

The catalysts of this invention comprise acidic molecular sieve, iridium and germanium. Molecular sieves include, but are not limited to, zeolite beta, zeolite MTW, zeolite Y (both cubic and hexagonal forms), zeolite X, mordenite, zeolite L, zeolite ferrierite, MFI, and erionite. Zeolite beta is described in U.S. Pat. No. 3,308,069 according to its structure, composition, and preferred methods of synthesis. Y zeolites are broadly defined in U.S. Pat. No. 3,130,007, which also includes synthesis and structural details. Mordenite is a naturally occurring siliceous zeolite which can have molecular channels defined by either 8 or 12 member rings. Donald W. Breck describes the structure and properties of mordenite in Zeolite Molecular Sieves (John Wiley and Sons, 1974, pp. 122-124 and 162-163). Zeolite L is defined in U.S. Pat. No. 3,216,789, which also provides information on its unique structure as well as its synthesis details. Other examples of zeolites that can be used are those having known structure types, as classified according to their three-letter designation by the Structure Commission of the International Zeolite Association ("Atlas of Zeolite Structure Types", by Meier, W. M.; Olsen, D. H; and Baerlocher, Ch., 1996) of MFI, FER, ERI, MTW and FAU. Zeolite X is a specific example of the latter structure type. The preferred molecular sieves are acidic molecular sieves having a pore size of at least about 6 Angstroms, say 6 to 12, Angstroms. Mordenite is one specific type of preferred molecular sieves. The molecular sieves useful in this invention include those that are treated after synthesis, e.g., by dealumination, exchange, and calcination.

A refractory binder or matrix is optionally utilized to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica.

The molecular sieve may be present in a range from 5 to 99 mass percent of the catalyst and the refractory inorganic oxide may be present in a range of from about 1 to 95 mass percent. Alumina is an especially preferred inorganic oxide binder.

The catalyst also contains iridium. Iridium may exist within the final catalytic composite as a compound such as an oxide or sulfide or in chemical combination with one or more of the other ingredients of the composite, or, preferably, as an elemental metal. This component may be present in the final catalyst composite in any amount which is catalytically effective, generally comprising at least about 0.01, preferably less than about 0.3, say 0.05 to 0.25, mass percent of the final catalyst calculated on an elemental basis. The iridium component may be incorporated into the catalyst in any suitable manner such as comulling, coprecipitation or cogelation with the carrier material, ion exchange or impregnation.

The catalyst contains germanium. The ratio of germanium to iridium is important to obtaining an active transalkylation catalyst that attenuates the co-production of naphthenes and lights. The amount of germanium should be sufficient that under Evaluation Conditions, a Ring Loss of less than about 1.25 mass percent is achieved. Often the atomic ratio of germanium to iridium is at least about 5:1, say, 5:1 to 50:1, and preferably between about 8:1 to 40:1.

The germanium component may be incorporated into the catalyst in any suitable manner such as comulling, coprecipitation or cogelation with the carrier material, ion exchange or impregnation. Frequently, water or alcohol soluble compounds of the metal are used for the impregnation. The incorporation of germanium into the catalyst may precede, follow or be simultaneous with the incorporation of the iridium component.

The catalyst may optionally contain an additional modifier component. Preferred additional metal modifier components of the catalyst include, for example, tin, lead, indium, and mixtures thereof. Catalytically effective amounts of such metal modifiers may be incorporated into the catalyst by any suitable manner. A preferred amount is a range of about 0.01 to about 2.0 mass percent on an elemental basis.

Generally, water may have a deleterious effect on the catalyst and prolonged contact with the catalyst will cause a loss of activity as described in U.S. Pat. No. 5,177,285 and U.S. Pat. No. 5,030,786. Thus, a typically low water concentration of less than about 200 wt-ppm results in reasonable operation.

EXAMPLES

In the following examples, all parts and percentages of liquids and solids are by mass and those of gases are molar, unless otherwise stated or apparent from the context. The following examples are illustrative only and are not in limitation of the broad aspects of the invention.

Example 1

A series of supported catalysts are prepared using the following procedure. An impregnating solution containing appropriate amounts of metal components to provide the desired metal content in the final catalyst is added to the container. Each impregnating solution is made using appropriate amounts of one or more of the following stock reagents to provide the sought metal content on the catalyst:

Hydrogen hexachloroiridate ($H_2IrCl_6$) in water, 2.75%-mass Ir

Perrhenic acid ($HReO_4$) in water, 1.07%-mass Re

Palladium Chloride ($PdCl_2$) in water, 0.53%-mass Pd

Germanium ethoxide ($Ge(OCH_2CH_3)_4$) in 1-propanol, 0.75%-mass Ge.

Distilled water is added to each impregnating solution to provide about 7.4 milliliters of impregnating solution per gram of support. A mordenite support material containing 75 weight parts mordenite (H-MOR) and 25 weight parts gamma alumina as binder is placed in the container. The mordenite has a silica to alumina ratio of about 20:1. The particle size of the support is that sieved to the range of about 0.25 to 0.43 millimeter. The mixture is dried in a rotary evaporator until free-flowing. The impregnated catalyst is then dried in air at about 100° C. for about one hour and calcined in air at about 510° C. for about 6 hours.

The catalysts are evaluated for transalkylation properties with a feedstock comprising 50 mole percent toluene, 25 mole percent 1,3,5-trimethylbenzene, and 25 mole percent 4-ethyltoluene. The evaluation is conducted under a pressure of about 2800 kPa absolute, a weight hourly space velocity of about 3 hr$^{-1}$ and the conditions set forth in Table I. The performance results are also provided in Table I.

Distilled water is added to each impregnating solution to provide about an equal volume to the volume of the support. A mordenite support material containing 75 weight parts mordenite (H-MOR) and 25 weight parts gamma alumina as binder is placed in the container. The mordenite has a silica to alumina ratio of about 20:1. The support is cylindrical pellet having a diameter of about 1.6 millimeters and a length to diameter ratio of about 4. The mixture is dried in a rotary evaporator by cold rolling until free-flowing. The impregnated catalyst is then dried in air at about 100° C. for about one hour and calcined in air at about 510° C. for about 6 hours.

TABLE I

| Catalyst | Temp. °C. | H$_2$:HC | Catalyst Main Metal, % mass | | | Ge % mass | Performance MEB Conversion Mole % | Xylene Selectivity Mole % | C6 + NA Make Mole % |
| | | | Ir | Pd | Re | | | | |
|---|---|---|---|---|---|---|---|---|---|
| A (COMP) | 350 | 3 | 0.1 | 0 | 0 | 0 | 64 | 70 | 1 |
| B | 350 | 3 | 0.1 | 0 | 0 | 0.3 | 80 | 67 | 2.5 |
| C | 350 | 3 | 0.1 | 0 | 0 | 0.5 | 78 | 68 | 2 |
| D (COMP) | 350 | 3 | 0.3 | 0 | 0 | 0 | 80 | 57 | 10 |
| E (COMP) | 350 | 3 | 0.3 | 0 | 0 | 0.3 | 87 | 63 | 5 |
| F | 350 | 3 | 0.3 | 0 | 0 | 0.5 | 87 | 65 | 3 |
| G (COMP) | 350 | 3 | 0 | 0.1 | 0 | 0 | 82 | 58 | 7.5 |
| H (COMP) | 350 | 3 | 0 | 0.1 | 0 | 0.3 | 62 | 67 | 1 |
| I (COMP) | 350 | 3 | 0 | 0.1 | 0 | 0.5 | 50 | 70 | 1 |
| J (COMP) | 350 | 3 | 0 | 0 | 0.1 | 0 | 78 | 66 | 2 |
| K (COMP) | 350 | 3 | 0 | 0 | 0.1 | 0.3 | 76 | 67 | 1.2 |
| L (COMP) | 350 | 3 | 0 | 0 | 0.1 | 0.5 | 83 | 68 | 1.8 |

The results provided in Table I illustrate that germanium, when used in a sufficient amount in comparison to iridium, can enhance conversion while maintaining desirably low total benzene and non-aromatics make (C6+NA). However, where the elemental ratio of germanium to iridium is too low, regardless of how much germanium is present, the C6+NA make increases.

Germanium, as shown in the results summarized in Table I, does not have a similar effect on palladium or rhenium, both of which have been proposed for transalkylation catalysts.

Example 2

Another series of supported catalysts are prepared using the following procedure. An impregnating solution containing appropriate amounts of metal components to provide the desired metal content in the final catalyst is added to the container. Each impregnating solution is made using appropriate amounts of one or more of the following stock reagents to provide the sought metal content on the catalyst:

Hydrogen hexachloroiridate (H$_2$IrCl$_6$) in water, 2.75%-mass Ir

Germanium ethoxide (Ge(OCH$_2$CH$_3$)$_4$) in 1-propanol, 0.75%-mass Ge

Table II describes the catalysts.

TABLE II

| CATALYST | Ir, %-mass | Ge, %-mass |
|---|---|---|
| M (COMP) | 0.2 | 0 |
| N | 0.1 | 0.5 |
| P | 0.3 | 0.5 |
| Q (COMP) | 0.2 | 0.2 |
| R | 0.2 | 0.6 |
| S | 0.2 | 1 |

Example 3

The catalysts prepared in Example 2 are evaluated for transalkylation activity. The feed contains:

| Toluene: | 74.7%-mass |
|---|---|
| Trimethylbenzene: | 9.6%-mass |
| Methylethylbenzene: | 9.9%-mass |
| Diethylbenzene | 0.4%-mass |
| Dimethylethylbenzene | 1.1%-mass |
| Other | balance |

The weight hourly space velocity is about 4 hr$^{-1}$, pressure is about 1725 kPa (gauge), and hydrogen is provided in an amount to provide a hydrogen to hydrocarbon ratio of about 5.8:1.

The results of the evaluation are summarized in Table III.

TABLE III

| CATALYST | TEMP, ° C. | Performance | | |
|---|---|---|---|---|
| | | Overall Conversion %-mass | MEB conversion %-mass | Aromatic Ring Loss %-mass |
| M | 338 | 19.1 | 23.8 | 0.51 |
| | 349 | 24.4 | 32.0 | 0.66 |
| | 362 | 30.4 | 42.2 | 0.88 |
| | 371 | 35.9 | 52.6 | 1.11 |
| N | 338 | 28.7 | 44.4 | 1.00 |
| | 349 | 35.3 | 57.2 | 1.33 |
| | 362 | 68.7 | 68.7 | 1.87 |
| | 371 | 78.2 | 78.2 | 2.46 |
| P | 338 | 32.5 | 52.4 | 1.77 |
| | 349 | 39.2 | 65.6 | 2.43 |
| | 362 | 44.6 | 76.7 | 3.37 |
| | 371 | 48.7 | 84.8 | 4.64 |
| Q | 338 | 31.5 | 47.9 | 1.59 |
| | 349 | 38.1 | 60.9 | 2.21 |
| | 362 | 43.6 | 72.8 | 3.01 |
| | 371 | 47.7 | 81.4 | 4.10 |
| R | 338 | 27.8 | 44.4 | 0.94 |
| | 349 | 35.3 | 57.2 | 1.33 |
| | 362 | 40.8 | 68.7 | 1.87 |
| | 371 | 45.1 | 78.2 | 2.59 |
| S | 338 | 26.3 | 40.8 | 1.06 |
| | 349 | 33.0 | 54.1 | 1.50 |
| | 362 | 39.4 | 66.5 | 2.14 |
| | 371 | 44.2 | 76.3 | 2.94 |

The performance summarized in Table III confirms that germanium can significantly improve the activity of an iridium-containing transalkylation catalyst while maintaining a relatively low ring loss, provided that germanium is present in a sufficient ratio with respect to iridium.

What is claimed is:

1. A catalyst suitable for the transalkylation of alkylaromatic compounds comprising a catalytically effective amount of acidic molecular sieve, at least about 0.01 mass percent iridium calculated on an elemental basis, and germanium wherein germanium is provided in a sufficient atomic ratio to iridium to achieve, under Evaluation Conditions, a Ring Loss of less than about 1.25 mass percent.

2. The catalyst of claim 1 in which the acidic molecular sieve comprises mordenite.

3. The catalyst of claim 2 in which the mole ratio of germanium to iridium is at least about 5:1.

4. The catalyst of claim 3 in which the iridium is in an amount of less than about 0.3 mass percent.

5. The catalyst of claim 4 in which the iridium is in an amount of between about 0.05 and 0.25 mass percent.

6. A catalyst suitable for the transalkylation of alkylaromatic compounds comprising a catalytically effective amount of acidic molecular sieve, a catalytically effective amount of iridium said amount being less than about 0.3 mass percent iridium calculated on an elemental basis, and germanium in an atomic ratio of germanium to iridium of at least about 5:1.

7. The catalyst of claim 6 in which the acidic molecular sieve has a pore size of at least about 6 Angstroms.

8. The catalyst of claim 7 in which the atomic ratio of germanium to iridium is between about 5:1 and 50:1.

9. The catalyst of claim 8 in which the atomic ratio of germanium to iridium is between about 8:1 to 40:1.

10. The catalyst of claim 7 comprising a binder and mordenite, wherein mordenite is in an amount of between about 5 to 95 mass percent based upon the mass of the catalyst.

* * * * *